(12) United States Patent
Cole et al.

(10) Patent No.: US 11,724,972 B2
(45) Date of Patent: Aug. 15, 2023

(54) COMBINED PROCESS FOR ALKYLATION OF LIGHT OLEFINS USING IONIC LIQUID CATALYSTS

(71) Applicant: UOP LLC, Des Plaines, IL (US)

(72) Inventors: Matthew C. Cole, Evanston, IL (US); Dominic P. Weber, Windsor, CO (US); Rajeswar R. Gattupalli, Buffalo Grove, IL (US); Hye Kyung Timken, Albany, CA (US); Huping Luo, Moraga, CA (US); Bong Kyu Chang, Novato, CA (US); Rebecca Mudrock, Wauconda, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 17/935,962

(22) Filed: Sep. 28, 2022

(65) Prior Publication Data

US 2023/0183150 A1 Jun. 15, 2023

Related U.S. Application Data

(60) Provisional application No. 63/265,434, filed on Dec. 15, 2021.

(51) Int. Cl.
| | |
|---|---|
| *C07C 2/60* | (2006.01) |
| *B01J 31/02* | (2006.01) |
| *C07C 2/58* | (2006.01) |
| *C07C 2/62* | (2006.01) |

(52) U.S. Cl.
CPC .............. *C07C 2/60* (2013.01); *B01J 31/0284* (2013.01); *C07C 2/58* (2013.01); *C07C 2/62* (2013.01); *B01J 2231/30* (2013.01); *C07C 2531/02* (2013.01)

(58) Field of Classification Search
None
See application file for complete search history.

(56) References Cited

U.S. PATENT DOCUMENTS

| | | | | |
|---|---|---|---|---|
| 3,236,912 A | * | 2/1966 | Phillips ...................... | C07C 9/16 585/331 |
| RE28,724 E | * | 2/1976 | Sobel ........................ | C07C 2/62 585/722 |
| 5,817,908 A | * | 10/1998 | Mehlberg .................. | C07C 2/54 585/731 |

(Continued)

OTHER PUBLICATIONS

U.S. Appl. No. 17/954,420.
U.S. Appl. No. 17/954,438.
U.S. Appl. No. 17/954,486.

*Primary Examiner* — Ali Z Fadhel (57) ABSTRACT

Processes for the direct alkylation of ethylene with isobutane or isopentane using a highly active ionic liquid alkylation catalyst are described. Ethylene is sent to a high-temperature alkylation reactor loop, and $C_3$, $C_4$, and $C_5$ olefins are routed to a low temperature alkylation reactor loop. In each reactor, the olefins are contacted with an excess of isobutane or isopentane in the presence of a highly active ionic liquid catalyst. Portions of the reactor effluent streams are fed to a common downstream catalyst separation and product fractionation sections. The remainder of the reactor effluent is recycled back to the respective alkylation reactor.

19 Claims, 1 Drawing Sheet

(56) References Cited

U.S. PATENT DOCUMENTS

| | | | |
|---|---|---|---|
| 5,849,965 A * | 12/1998 | Mehlberg | C07C 2/62 585/458 |
| 6,194,625 B1 * | 2/2001 | Graves | C07C 2/62 502/29 |
| 7,432,408 B2 | 10/2008 | Timken et al. | |
| 7,432,409 B2 | 10/2008 | Elomari et al. | |
| 7,651,970 B2 | 1/2010 | Elomari et al. | |
| 7,674,739 B2 | 3/2010 | Elomari et al. | |
| 7,674,740 B2 | 3/2010 | Harris et al. | |
| 7,678,727 B2 | 3/2010 | Harris et al. | |
| 7,691,771 B2 | 4/2010 | Harris et al. | |
| 7,727,925 B2 | 6/2010 | Elomari et al. | |
| 7,732,363 B2 | 6/2010 | Elomari et al. | |
| 7,737,067 B2 | 6/2010 | Elomari et al. | |
| 7,825,055 B2 | 11/2010 | Elomari et al. | |
| 7,956,002 B2 | 6/2011 | Elomari et al. | |
| 8,524,623 B2 | 9/2013 | Timken et al. | |
| 9,079,175 B1 | 7/2015 | Smith et al. | |
| 9,079,176 B1 | 7/2015 | Smith et al. | |
| 9,120,092 B1 | 9/2015 | Broderick et al. | |
| 9,221,043 B2 | 12/2015 | Broderick et al. | |
| 2006/0131209 A1 * | 6/2006 | Timken | C10L 1/06 208/16 |
| 2006/0135839 A1 * | 6/2006 | Elomari | C10G 29/205 585/709 |
| 2007/0299292 A1 * | 12/2007 | Cross | C10G 29/205 585/720 |
| 2008/0045763 A1 * | 2/2008 | Cross | C10G 57/02 585/332 |
| 2009/0306448 A1 * | 12/2009 | Smith, Jr. | C07C 2/62 585/520 |
| 2011/0319693 A1 * | 12/2011 | Hommeltoft | C07C 2/60 585/711 |
| 2012/0088948 A1 * | 4/2012 | Mukherjee | B01J 29/90 585/722 |

* cited by examiner

COMBINED PROCESS FOR ALKYLATION OF LIGHT OLEFINS USING IONIC LIQUID CATALYSTS

RELATED APPLICATIONS

This application claims priority to U.S. Provisional Patent Application Ser. No. 63/265,434, filed on Dec. 15, 2021, the entirety of which is incorporated herein by reference.

As environmental regulations on motor gasoline continue to tighten, refiners' ability to maximize production of high-octane, low-contaminant gasoline for pool blending economically becomes increasingly important. A key blending component used to improve the quality of the gasoline pool has long been alkylate derived from excess propylene and butylene. Adding ethylene as a feedstock to the alkylation unit would allow refiners to increase the amount of alkylate produced economically and to recover more value from small olefinic cracked byproducts.

However, the direct alkylation of ethylene has not been possible with traditional alkylation catalysts and processes previously due to the relatively slow kinetics of the reaction. Efforts to produce alkylate from ethylene have relied on dimerizing ethylene to butylene in a dimerization process unit, followed by alkylation with isobutane in the alkylation process unit. This method requires significant extra capital investment for the dimerization unit. In addition, alkylate yield per barrel of ethylene is very low.

Therefore, there is a need for an improved process for alkylation of light olefins.

DESCRIPTION OF THE INVENTION

The current invention solves this problem by providing a process for the direct alkylation of ethylene with isobutane or isopentane using a highly active ionic liquid alkylation catalyst. This process can be carried out in an ionic liquid alkylation unit that also processes propylene, butylenes, and amylenes, eliminating the need for a separate ethylene dimerization unit. As a result, the process drastically reduces capital costs and offers a significant economic advantage over the dimerization process. Furthermore, the direct alkylation of ethylene and isobutane to high-octane 2,3-dimethylbutane is much more efficient than the dimerization method in producing $C_8$ alkylate with similar octane. The yield for the direct alkylation process is about 1.6 barrels of alkylate per barrel of ethylene feed compared to approximately 1.1 barrels of alkylate per barrel of ethylene feed for the dimerization method. This yield advantage will allow refiners to produce more alkylate with the same amount of ethylene feed, further increasing the value of the process.

The process involves feeding $C_2$ to $C_5$ olefins to an ionic liquid alkylation unit. Ethylene is sent to a high-temperature alkylation reactor loop (30° C.-100° C.), and the $C_3$, $C_4$, and $C_5$ olefins are routed to a low temperature alkylation reactor loop (0° C. 35° C.). In each reactor, the olefins are contacted with an excess of isobutane or isopentane in the presence of a highly active ionic liquid catalyst. The conversion of olefin to alkylate is nearly 100% in the reactors. The resulting reactor effluents comprise ionic liquid, unreacted isoparaffin, and alkylate. Portions of the reactor effluent streams (e.g., 5% to 50%, or 10% to 25%) are withdrawn from each reactor recycle loop and are fed to the common downstream catalyst separation and product fractionation sections. The remainder of the reactor effluent is recycled back to the respective alkylation reactor, optionally passing through a heat exchanger to heat or cool the stream if needed before entering the reactor. Each recycle stream may optionally be combined with fresh olefin feed and recycled isoparaffin returning from the unit's fractionation section. The ionic liquid catalyst recovered in the catalyst separation section may also be recycled back to the alkylation reactors. A slip stream of the catalyst recycle may be sent to a catalyst regeneration unit to remove conjunct polymer built up within the ionic liquid.

The term "alkylate" means the reaction products generated in alkylation reactions between an olefin and an isoparaffin in the presence of a catalyst. Alkylates typically are highly branched paraffinic hydrocarbons. Refiners can use alkylate as a gasoline blend stock to boost octane, reduce Reid vapor pressure (RVP), and reduce olefin content in a final gasoline blend.

The term "$C_n$" means a hydrocarbon compound having n number of carbon atoms per molecule. Similarly, the term "$C_{n-}$" means a hydrocarbon compound having n or less than n carbon atoms per molecule. The term "$C_{n+}$" means a hydrocarbon compound having n or more than n carbon atoms per molecule.

The term "octane number" refers to the percentage of iso-octane in a mixture of iso-octane and n-heptane that would have the same knock resistance as the presently tested fuel, according to ASTM D2699 and D2700. Octane numbers typically range from 0 to 100, with higher values indicating better fuel performance. Octane numbers are unitless.

The term "Research Octane Number" (RON) refers to the octane number obtained by testing at lower engine speed and temperature, typically about 600 rpm, according to ASTM D2699.

The term "weight percent", "wt. %", "percent by weight", "% by weight", and variations thereof, as used herein, refer to the concentration of a substance as the weight of that substance divided by the total weight of the composition and multiplied by 100. It is understood that, as used herein, "percent", "%" and the like are intended to be synonymous with "weight percent", "wt. %", etc.

As used herein, the terms "unit," "zone," and "section" can refer to an area including one or more equipment items as appropriate for the type of unit, zone, or section and/or one or more sub-zones or sub-sections. Equipment items can include, but are not limited to, one or more reactors or reactor vessels, separation vessels, adsorbent chamber or chambers, distillation towers, heaters, exchangers, pipes, pumps, compressors, and controllers. Additionally, an equipment item, such as a reactor, dryer, adsorbent chamber, or vessel, can further include one or more sections, sub-sections, zones, or sub-zones.

The term "about" means within 10% of the value stated, or within 5%, or within 1%.

One aspect of the invention is an integrated process for ionic liquid alkylation of $C_2$ to $C_5$ olefins. In one embodiment, the process comprises: reacting an ethylene feed stream comprising ethylene and an isoparaffin feed stream comprising isobutane in the presence of an ionic liquid catalyst comprising an ionic liquid in a high-temperature alkylation reactor under first alkylation reaction conditions to form a first alkylation effluent stream comprising the first ionic liquid, the isoparaffin, and alkylate, wherein the first alkylation reaction conditions comprise a temperature in a range of 30° C. to 100° C. and a pressure in a range of 100 psig to 1000 psig; reacting a $C_3$-$C_5$ olefin feed stream comprising olefins having 3 to 5 carbon atoms and a second isoparaffin feed stream comprising isobutane in the presence of the ionic liquid catalyst in a low temperature alkylation reactor under second alkylation reaction conditions to form a second alkylation effluent stream comprising the second ionic liquid, the isoparaffin, and alkylate, wherein the second alkylation reaction conditions comprise a temperature in a range of 0° C. to 35° C. and a pressure in a range of 40 psig to 300 psig; combining a first portion of the first alkylation effluent stream and a first portion of the second alkylation effluent streams to form a combined stream; separating the combined stream into an ionic liquid recycle stream comprising the ionic liquid and a hydrocarbon stream comprising the isoparaffin and the alkylate; separating the hydrocarbon stream into an isoparaffin recycle stream comprising the isoparaffin and an alkylate stream comprising the alkylate; and recovering the alkylate stream.

In some embodiments, the process further comprises: dividing the first alkylation effluent stream into the first portion and a second portion; heating the second portion of the first alkylation effluent stream and recycling the heated second portion of the first alkylation effluent stream to the high temperature alkylation reactor; dividing the second alkylation effluent stream into the first portion and a second portion; cooling the second portion of the second alkylation effluent stream and recycling the cooled second portion of the second alkylation effluent stream to the low temperature alkylation reactor.

In some embodiments, the process further comprises: recycling the isoparaffin recycle stream to the high temperature alkylation reactor, the low temperature reactor, or both.

In some embodiments, the process further comprises: recycling the ionic liquid recycle stream to the high temperature alkylation reactor, the low temperature reactor, or both.

In some embodiments, the process further comprises: regenerating a portion of the ionic liquid recycle stream to form a regenerated ionic liquid stream; recycling the regenerated ionic liquid stream to the high temperature alkylation reactor, the low temperature reactor, or both.

In some embodiments, the process further comprises: treating an ethylene stream to remove contaminants to form a treated ethylene stream, wherein the treated ethylene stream comprises the ethylene feed stream; treating a $C_3$-$C_5$ olefin stream comprising olefins having 3 to 5 carbon atoms to remove contaminants to form a treated $C_3$-$C_5$ olefin stream, wherein the treated $C_3$-$C_5$ olefin stream comprises the $C_3$-$C_5$ olefin feed stream.

In some embodiments, the first alkylation reaction conditions comprise an overall paraffin to ethylene molar ratio of 2:1 to 20:1, and a residence time in a range of 5 minutes to 1 hr.

In some embodiments, the second alkylation reaction conditions comprise an overall paraffin to olefin molar ratio of 2:1 to 20:1, and a residence time in a range of 1 minute to 1 hr.

In some embodiments, the ionic liquid comprises an organic cation and a halometallate anion and wherein the organic cation comprises an ammonium cation, a pyrrolidinium cation, a pyridinium cation, an imidazolium, a phosphonium cation, or a combination thereof.

In some embodiments, the ionic liquid comprises an organic cation and a halometallate anion and wherein the halometallate anion comprises a metal selected from Al, Ga, In, Mn, Fe, Co, Ni, Cu, Zn, or a combination thereof, and a halide selected from F, Cl, Br, I, or a combination thereof.

In some embodiments, the process includes one or more of: the ionic liquid is present in an amount of from 5 vol % to 60 vol % of a total volume of material in the high temperature alkylation reactor; the ionic liquid is present in an amount of from 1 vol % to 10 vol % of a total volume of material in the low temperature alkylation; and the ionic liquid is present in an amount of from 1 vol % to 60 vol % of a total volume of material in the combined stream.

In some embodiments, the alkylate in the alkylate stream has a research octane number (RON) of 90 or more, or 92 or more, or 93 or more, or 94 or more, or 95 or more, or 96 or more, or 97 or more, or 98 or more, or 99 or more, or 100 or more.

Another aspect of the invention is an integrated process for ionic liquid alkylation of $C_2$ to $C_5$ olefins. In one embodiment, the process comprises: reacting an ethylene feed stream comprising ethylene and an isoparaffin feed stream comprising isobutane with an ionic liquid catalyst comprising an ionic liquid in a high temperature alkylation reactor under first alkylation reaction conditions to form a first alkylation effluent stream comprising the first ionic liquid, the isoparaffin, and alkylate, wherein the first alkylation reaction conditions comprise a temperature in a range of 30° C. to 100° C., a pressure in a range of 100 psig to 1000 psig, an overall paraffin to ethylene molar ratio of 2:1 to 20:1, and a residence time in a range of 5 minutes to 1 hr; reacting a $C_3$-$C_5$ olefin feed stream comprising olefins having 3 to 5 carbon atoms and a second isoparaffin feed stream comprising isobutane with the ionic liquid catalyst in a low temperature alkylation reactor under second alkylation reaction conditions to form a second alkylation effluent stream comprising the second ionic liquid, the isoparaffin, and alkylate, wherein the second alkylation reaction conditions comprise a temperature in a range of 0° C. to 35° C., comprise a pressure in a range of 40 psig to 300 psig, an overall paraffin to olefin molar ratio of 2:1 to 20:1, and a residence time in a range of 1 minute to 1 hr; dividing the first alkylation effluent stream into a first portion and a second portion; heating the second portion of the first alkylation effluent stream and recycling the heated second portion of the first alkylation effluent stream to the high temperature alkylation reactor; dividing the second alkylation effluent stream into a first portion and a second portion; cooling the second portion of the second alkylation effluent stream and recycling the cooled second portion of the second alkylation effluent stream to the low temperature alkylation reactor; combining the first portion of the first alkylation effluent stream and the first portion of the second alkylation effluent streams to form a combined stream; separating the combined stream into an ionic liquid recycle stream comprising the ionic liquid and a hydrocarbon stream comprising the isoparaffin and the alkylate; separating the hydrocarbon stream into an isoparaffin recycle stream comprising the isoparaffin and an alkylate stream comprising the alkylate; recycling the isoparaffin recycle stream to the high temperature alkylation reactor, the low temperature reactor, or both; recycling the ionic liquid recycle stream to the high temperature alkylation reactor, the low temperature reactor, or both; and recovering the alkylate stream.

In some embodiments, the process further comprises: regenerating a portion of the ionic liquid recycle stream to form a regenerated ionic liquid stream; recycling the regenerated ionic liquid stream to the high temperature alkylation reactor, the low temperature reactor, or both.

In some embodiments, the process further comprises: treating an ethylene stream to remove contaminants to form a treated ethylene stream, wherein the treated ethylene stream comprises the ethylene feed stream; treating a $C_3$-$C_5$ olefin stream comprising olefins having 3 to 5 carbon atoms to remove contaminants to form a treated $C_3$-$C_5$ olefin stream, wherein the treated $C_3$-$C_5$ olefin stream comprises the $C_3$-$C_5$ olefin feed stream.

In some embodiments, the ionic liquid comprises an organic cation and a halometallate anion and wherein the organic cation comprises an ammonium cation, a pyrrolidinium cation, a pyridinium cation, an imidazolium, a phosphonium cation, or a combination thereof.

In some embodiments, the ionic liquid comprises an organic cation and a halometallate anion and wherein the halometallate anion comprises a metal selected from Al, Ga, In, Mn, Fe, Co, Ni, Cu, Zn, or a combination thereof, and a halide selected from F, Cl, Br, I, or a combination thereof.

In some embodiments, the process comprises one or more of: the ionic liquid is present in an amount of from 10 vol % to 60 vol % of a total volume of material in the high temperature alkylation reactor; the ionic liquid is present in an amount of from 1 vol % to 10 vol % of a total volume of material in the low temperature alkylation; and the ionic liquid is present in an amount of from 1 vol % to 60 vol % of a total volume of material in the combined stream.

In some embodiments, the alkylate in the alkylate stream has a research octane number (RON) of 90 or more.

The isoparaffin feed stream to the high-temperature alkylation reactor generally comprises at least 50 wt. % isobutane (e.g., 50 wt. % to 99 wt. % isobutane, or 50 wt. % to 95 wt. % isobutane, or 55 wt. % to 90 wt. % isobutane, or at least 80 wt. % isobutane, or 80 wt. % to 98 wt. % isobutane, or 90 wt. % to 97 wt. % isobutane), with at least 90 wt. % (e.g., at least 99 wt. %) of the remainder comprising n-butane.

The isobutane feed may be substantially free of one or more of (i) butenes, including isobutene, (ii) $C_{5+}$ hydrocarbon, and (iii) $C_{3-}$ hydrocarbon. In this context, the term "substantially free" means the isobutane feed comprises less than or equal to 1.0 wt. % of the designated compounds (e.g., less than or equal to 0.1 wt. %, or less than or equal to 0.01 wt. %, or less than or equal to 0.001 wt. %).

The ethylene feed stream may include dilute ethylene streams, containing up to 50 wt. % ethylene, for example. In some aspects, the ethylene feed stream may include a low purity ethylene feed, including 60 wt. % to 95 wt. % ethylene. In other aspects, the ethylene feed stream may include high purity ethylene (95 wt. % to 99+wt. % ethylene).

The dilute ethylene stream may be derived from any number of refinery streams. The dilute ethylene stream may be an off-gas from a refinery unit selected from an ethylene cracker, a fluid catalytic cracker, a coker, a naphtha cracker, a Fischer-Tropsch synthesis unit, an ethylene polymerization unit, a pyrolysis unit, or the product of an ethanol dehydration unit.

The dilute ethylene stream may contain from 0.1 wt. % to 50 wt. % ethylene, such as from 5 wt. %, 10 wt. %, or 15 wt. % to 30 wt. %, 40 wt. %, or 50 wt. % ethylene. A suitable dilute ethylene stream may comprise from 5 wt. % to 50 wt. % ethylene. The balance of the dilute ethylene stream may include hydrogen, methane, ethane, propylene, and/or propane. For example, a typical FCC off-gas may include 50 wt. % to 70 wt. % methane and hydrogen, with the balance being about equal parts ethane and ethylene, as well as a minor amount of $C_{3+}$ compounds.

In some aspects, the ethylene feed stream may be a polymer-grade ethylene stream, which may have at least 98 wt. %, or at least 99 wt. %, or at least 99.5 wt. %, or at least 99.8 wt. % ethylene.

The ionic liquid catalyst comprises one or more ionic liquids. Any suitable ionic liquid can be used. Ionic liquids are salts comprised of cations and anions which typically melt below about 100° C. The ionic liquid comprises an organic cation and an anion. The organic cation is generally a nitrogen-based cation, a phosphorus-based cation, or a combination thereof. Representative organic cations include, but are not limited to, ammonium, pyrrolidinium, pyridinium, imidazolium, and phosphonium cations.

Examples of ammonium cations include, but are not limited to, tetraalkylammonium cations (e.g., tri $C_1$-$C_6$ alkyl-$C_2$-$C_{10}$ alkyl ammonium cations, such as trimethyl-n-propylammonium, n-butyl-trimethylammonium, n-hexyl-trimethylammonium, triethyl-methylammonium, tetraethylammonium, n-butyl-triethylammonium, and tetra-n-butylammonium).

Examples of pyrrolidinium cations include, but are not limited to, N,N-dialkylpyrrolidinium cations (e.g., N—$C_1$-$C_3$ alkyl-N—$C_2$-$C_6$ alkyl-pyrrolidinium cations, such as N-methyl-N-propylpyrrolidinium and N-butyl-N-methylpyrrolidinium.

Examples of imidazolium cations include, but are not limited to, 1,3-dialkylimidazolium cations (e.g., 1-$C_2$-$C_{10}$ alkyl-3-$C_1$-$C_3$ alkyl-imidazolium cations, such as 1-ethyl-3-methylimidazolium, 1-n-butyl-3-methylimidazolium, 1-n-hexyl-3-methylimidazolium, and 1-n-octyl-3-methylimidazolium), Examples of pyridinium cations include, but are not limited to, N-alkylpyridinium cations (e.g., N—$C_2$-$C_6$ alkyl-pyridinium cations, such as N-ethylpyridinium and N-butylpyridinium).

Examples of phosphonium cations include, but are not limited to, tetraalkylphosphonium cations (e.g., tri $C_1$-$C_{10}$ alkyl-$C_2$-$C_{20}$ alkylphosphonium cations, such as triethyl-pentylphosphonium, tetrabutylphosphonium, and trihexyl-tetradecylphosphonium).

The anion of the ionic liquid comprises a halometallate. Halometallate anions may contain a metal selected from Al, Ga, In, Mn, Fe, Co, Ni, Cu, Zn, or combinations thereof, and a halide selected from F, Cl, Br, I, or combinations thereof. In some aspects, the anion of the ionic liquid comprises a haloaluminate. In some aspects, the anion of the ionic liquid comprises a chloroaluminate. For catalytic applications requiring Lewis acidity (such as alkylation), the ratio of moles of halide to moles of metal in the halometallate anion is less than 4. The anion may be formally an anion, or it may be an anion associated with a metal halide. For instance, the anion may be $AlCl_4^-$ or $Al_2O_7^-$ associated with $AlCl_3$. The anion may be $GaCl_4^-$ or $Ga_2Cl_7^-$ or $Ga_3Cl_{10}^-$ associated with $GaCl_3$ The ionic liquid catalyst can include a co-catalyst (or catalyst promoter). to enhance the activity of the ionic liquid catalyst by boosting its overall acidity. The co-catalyst may be a Brønsted acid and/or a Brønsted acid precursor. The co-catalyst is present in an amount of 0.05 mol to 1 mol of co-catalyst per mol of ionic liquid, or 0.05 mol to 0.7 mol, or 0.05 mol to about 0.5 mol, or 0.1 mol to 0.7 mol, or 0.1 mol to 0.5 mol. Suitable Brönsted acids include, but are not limited to, HCl, HBr, HI, and combinations thereof. Instead of adding co-catalyst, a promoter or precursor can be added to make the co-catalyst in-situ. Suitable Brönsted acid precursors include, but are not limited to, 2-chlorobutane, 2-chloro-2-methylpropane, 1-chloro-2-methylpropane, 1-chlorobutane, 2-chloropropane, 1-chloropropane and other chloroalkanes (e.g., secondary or tertiary chloroalkanes), or combinations thereof. In another instance, the Brönsted acid precursors can be carbon tetrachloride, chloroform, methylene chloride, tetrachloroethylene or tetrachloropropene where more than one chloride atoms per molecule.

Typical ethylene alkylation reaction conditions include a temperature range of 30° C. to 100° C. The minimum temperature can be 30° C., or 35° C., or 40° C., or 45° C., or 50° C., or 55° C., or 60° C.; additionally, or alternatively, the maximum temperature can be 100° C., or 95° C., or 90° C., or 85° C., or 80° C., or 75° C., or 70° C. Generally, the temperature can be in a range from any minimum temperature disclosed herein to any maximum temperature disclosed herein. It is preferred to have the ionic liquid that maintains its liquid state through the operating temperature range.

The ethylene alkylation reaction can be conducted at a pressure of from 100 psig to 1000 psig (689 kPa to 6895 kPa), such as 300 psig to 700 psig (2068 kPa to 4826 kPa), or 350 psig to 500 psig (2413 kPa to 3447 kPa).

The residence time of the reactants in the high-temperature reactor is in a range of from a few seconds to several hours (e.g., 30 seconds to 1 hour, or 2 minutes to 30 minutes, or 2 minutes to 10 minutes, or 5 minutes to 1 hour, or 5 minutes to 30 minutes, 5 minutes to 10 minutes).

The volume of ionic liquid in the high-temperature reactor may be in a range of from 1 vol % to 75 vol % of the total volume of material in the reactor (ionic liquid and hydrocarbons), or 1 vol % to 70 vol %, or 1 vol % to 65 vol %, or 1 vol % to 60 vol %, or 1 vol % to 55 vol %, or 1 vol % to 50 vol %, or 1 vol % to 45 vol %, or 1 vol % to 40 vol %, or 1 vol % to 35 vol %, or 1 vol % to 30 vol %, or 1 vol % to 25 vol %, or 1 vol % to 20 vol %, or 1 vol % to 15 vol %, or 1 vol % to 10 vol %, or 1 vol % to 5 vol %. When the ionic liquid catalyst volume is less than 50%, the hydrocarbon is the continuous phase of the reaction mixture in the presence of ionic liquid catalyst droplets. When the ionic liquid catalyst volume exceeds 50%, then the ionic liquid is the continuous phase with hydrocarbon droplets.

Due to the low solubility of hydrocarbons in ionic liquids, isoparaffin-olefin alkylation, like most reactions in ionic liquids, is generally biphasic. The catalytic alkylation reaction is generally carried out in a mixed phase liquid-liquid system. The system can be a batch system, a semi-batch system, or a continuous system as is usual for aliphatic alkylation. Vigorous mixing is desirable to ensure good contact between the reactants and the catalyst.

The isoparaffin and olefin can be introduced in the reactor separately or as a mixture, in one or multiple locations. The molar ratio of isoparaffin to olefin is generally 20:1 or less, or 15:1 or less, or in a range of 2:1 to 20:1, or in a range of 2:1 to 15:1, or in a range of 2:1 to 10:1, or in a range of 5:1 to 20:1, or in a range of 5:1 to 15:1, or in a range of 5:1 to 10:1.

In a semi-batch system, the catalyst, optional co-catalyst, and at least a portion of the isoparaffin is introduced with no olefin present, followed by the olefin or a mixture of isoparaffin and olefin. In a semi-batch system, the olefin is added gradually over a period of time. The catalyst is measured in the reactor with respect to the amount of total olefins added over the course of the reaction, with a catalyst to olefin weight ratio in a range of from 0.1:1 to 10:1 (e.g., 0.2:1 to 5:1, or 0.5:1 to 2.5:1).

In a continuous system, the ionic liquid catalyst, the isoparaffin, the olefin, and optionally the catalyst promoter are added continuously. The catalyst, optional catalyst promoter, unreacted isoparaffin, and unreacted olefin are each removed continuously from the reaction zone along with alkylate product. The catalyst, catalyst promoter, unreacted isoparaffin, and/or unreacted olefin may be recycled. The olefin may be added to one or more locations in the reaction zone. It is preferable to add the olefin to multiple locations in the reaction zone. Adding olefin in multiple locations or spreading the olefin addition over a longer period of time results in the isoparaffin to olefin ratio measured in a specific location at a specific point in time to be higher. The isoparaffin to olefin ratio is defined as the cumulative amount of isoparaffin divided by the cumulative amount of olefin added across the entire reaction zone.

The $C_3$-$C_5$ olefin feed stream for the low-temperature alkylation reactor generally comprises at least 20 wt. % propylene, butenes, or pentenes, with at least 90 wt. % of the remainder comprising propane, isobutane, n-butane, isopentane, or n-pentane.

The $C_3$-$C_5$ olefin feed stream may be derived from any number of refinery streams. The $C_3$-$C_5$ olefin feed stream may be a product or off-gas stream from a fluid catalytic cracker or a paraffin dehydrogenation unit.

Typical $C_3$-$C_5$ olefin alkylation reaction conditions include a temperature range of 0° C. to 35° C. The minimum temperature can be 0° C., or 5° C., or 10° C., or 15° C., or 20° C., or 25° C., or 30° C.; additionally, or alternatively, the maximum temperature can be 35° C., or 30° C., or 25° C., or 20° C., or 15° C., or 10° C., or 5° C. Generally, the temperature can be in a range from any minimum temperature disclosed herein to any maximum temperature disclosed herein. It is preferred to have the ionic liquid that maintains its liquid state through the operating temperature range.

The isoparaffin feed stream, and the ionic liquid catalyst are as described above.

The $C_3$-$C_5$ olefin alkylation reaction can be conducted at a pressure of from 40 psig to 400 psig (276 kPa to 2758 kPa), such as 100 psig to 250 psig (689 kPa to 1724 kPa), or 40 psig to 150 psig (276 kPa to 1034 kPa).

The residence time of the reactants in the low-temperature reactor is in a range of from a few seconds to several minutes (e.g., 10 seconds to 10 minutes, or 30 seconds to 30 minutes, or 1 minutes to 20 minutes, or 1 minute to 5 minutes).

The volume of ionic liquid in the low-temperature reactor may be in a range of from 1 vol % to 75 vol % of the total volume of material in the reactor (ionic liquid and hydrocarbons), or 1 vol % to 70 vol %, or 1 vol % to 65 vol %, or 1 vol % to 60 vol %, or 1 vol % to 55 vol %, or 1 vol % to 50 vol %, or 1 vol % to 45 vol %, or 1 vol % to 40 vol %, or 1 vol % to 35 vol %, or 1 vol % to 30 vol %, or 1 vol % to 25 vol %, or 1 vol % to 20 vol %, or 1 vol % to 15 vol %, or 1 vol % to 10 vol %, or 1 vol % to 5 vol %. When the ionic liquid catalyst volume is less than 50%, the hydrocarbon is the continuous phase of the reaction mixture in the presence of ionic liquid catalyst droplets. When the ionic liquid catalyst volume exceeds 50%, then the ionic liquid is the continuous phase with hydrocarbon droplets.

The isoparaffin and olefin can be introduced in the low-temperature reactor separately or as a mixture, in one or multiple locations. The molar ratio of isoparaffin to olefin is generally 20:1 or less, or 15:1 or less, or in a range of 2:1 to 20:1, or in a range of 2:1 to 15:1, or in a range of 2:1 to 10:1, or in a range of 5:1 to 20:1, or in a range of 5:1 to 15:1, or in a range of 5:1 to 10:1.

A portion of the effluent from the high-temperature reactor and the effluent from the low-temperature reactor (for example, 10-20% of each of the effluent streams, with the remainder being recycled to the respective alkylation reactor) are separated in an ionic liquid separation zone. The ionic liquid separation zone may be any suitable zone for separating the hydrocarbon phase and the ionic liquid phase. Suitable ionic liquid separation zones include, but are not limited to, gravity settlers, coalescers, filtration zones comprising sand or carbon, adsorption zones, scrubbing zones, or combinations thereof.

The hydrocarbon stream from the ionic liquid separation zone is sent to a hydrocarbon separation zone for separating the unreacted isoparaffin from the alkylate. Suitable hydrocarbon separation zones include, but are not limited to, distillation and vaporization.

The recycled ionic liquid may contain conjunct polymer which needs to be removed. A variety of methods for regenerating ionic liquids have been developed. For example, U.S. Pat. Nos. 7,651,970; 7,825,055; 7,956,002; and 7,732,363, each of which is incorporated herein by reference, describe contacting ionic liquid containing the conjunct polymer with a reducing metal (e.g., Al), an inert hydrocarbon (e.g., hexane), and hydrogen and heating to about 100° C. to transfer the conjunct polymer to the hydrocarbon phase, allowing for the conjunct polymer to be removed from the ionic liquid phase. Another method involves contacting ionic liquid containing conjunct polymer with a reducing metal (e.g., Al) in the presence of an inert hydrocarbon (e.g., hexane) and heating to about 100° C. to transfer the conjunct polymer to the hydrocarbon phase, allowing for the conjunct polymer to be removed from the ionic liquid phase. See e.g., U.S. Pat. No. 7,674,739 B2; which is incorporated herein by reference. Still another method of regenerating the ionic liquid involves contacting the ionic liquid containing the conjunct polymer with a reducing metal (e.g., Al), HCl, and an inert hydrocarbon (e.g., hexane), and heating to about 100° C. to transfer the conjunct polymer to the hydrocarbon phase. See e.g., U.S. Pat. No. 7,727,925, which is incorporated herein by reference. The ionic liquid can be regenerated by adding a homogeneous metal hydrogenation catalyst (e.g., $(PPh_3)_3RhCl$) to ionic liquid containing conjunct polymer and an inert hydrocarbon (e.g., hexane), and introducing hydrogen. The conjunct polymer is reduced and transferred to the hydrocarbon layer. See e.g., U.S. Pat. No. 7,678,727, which is incorporated herein by reference. Another method for regenerating the ionic liquid involves adding HCl, isobutane, and an inert hydrocarbon to the ionic liquid containing the conjunct polymer and heating to about 100° C. The conjunct polymer reacts to form an uncharged complex, which transfers to the hydrocarbon phase. See e.g., U.S. Pat. No. 7,674,740, which is incorporated herein by reference. The ionic liquid could also be regenerated by adding a supported metal hydrogenation catalyst (e.g., Pd/C) to the ionic liquid containing the conjunct polymer and an inert hydrocarbon (e.g., hexane). Hydrogen is introduced and the conjunct polymer is reduced and transferred to the hydrocarbon layer. See e.g., U.S. Pat. No. 7,691,771, which is incorporated herein by reference. Still another method involves adding a suitable substrate (e.g., pyridine) to the ionic liquid containing the conjunct polymer. After a period of time, an inert hydrocarbon is added to wash away the liberated conjunct polymer. The ionic liquid precursor [butylpyridinium][Cl] is added to the ionic liquid (e.g. [butylpyridinium][$Al_2Cl_7$]) containing the conjunct polymer followed by an inert hydrocarbon. After mixing, the hydrocarbon layer is separated, resulting in a regenerated ionic liquid. See, e.g., U.S. Pat. No. 7,737,067, which is incorporated herein by reference. Another method involves adding ionic liquid containing conjunct polymer to a suitable substrate (e.g., pyridine) and an electrochemical cell containing two aluminum electrodes and an inert hydrocarbon. A voltage is applied, and the current measured to determine the extent of reduction. After a given time, the inert hydrocarbon is separated, resulting in a regenerated ionic liquid. See, e.g., U.S. Pat. No. 8,524,623, which is incorporated herein by reference. Ionic liquids can also be regenerated by contacting with silane compounds (U.S. Pat. No. 9,120,092), borane compounds (U.S. Pat. No. 9,221,043), Brönsted acids, (U.S. Pat. No. 9,079,176), or $C_1$ to $C_{10}$ paraffins (U.S. Pat. No. 9,079,175), each of which is incorporated herein by reference.

Figure 1:
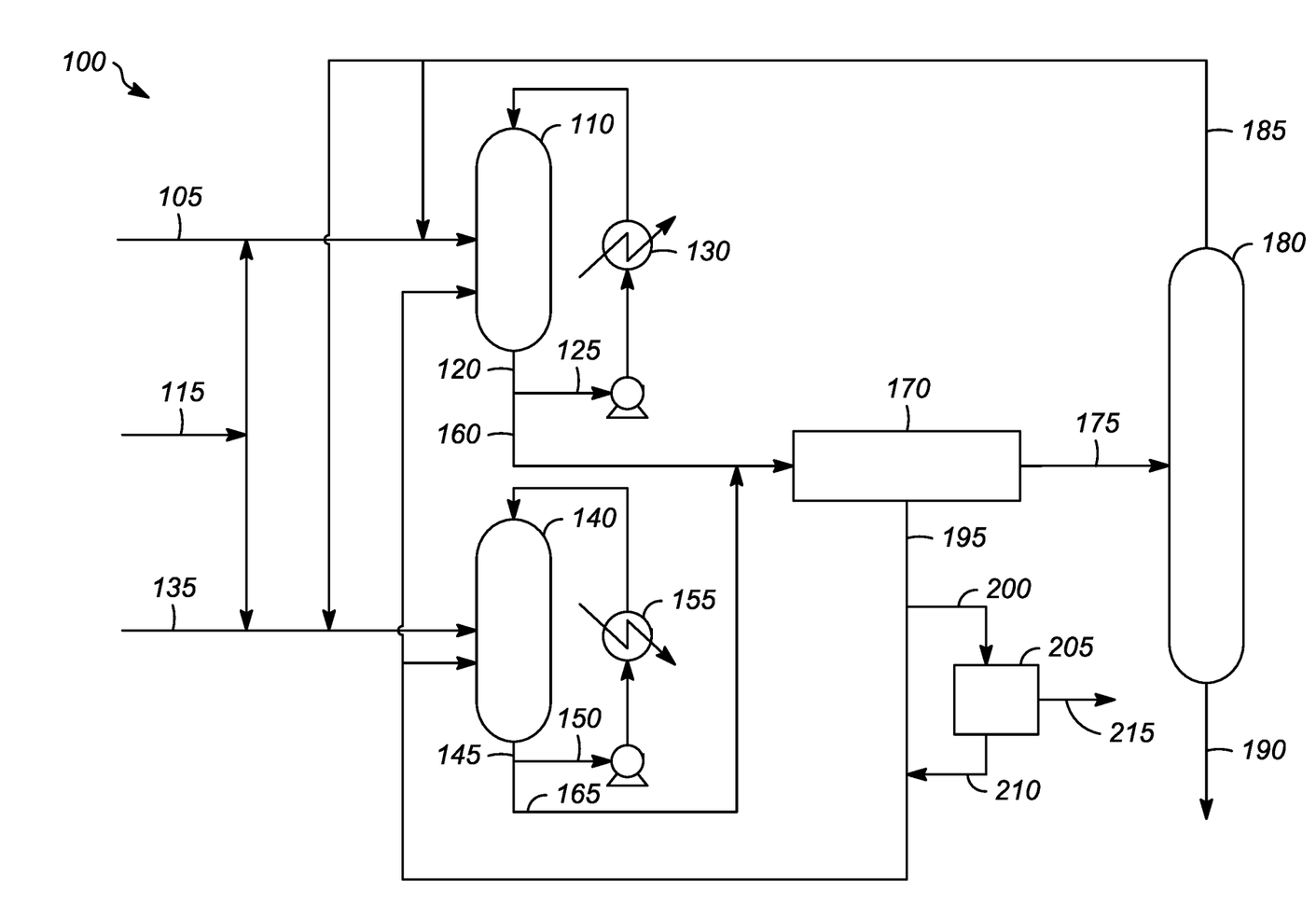
The FIGURE is an illustration of one embodiment of the process of the present invention.

The FIGURE illustrates one embodiment of the combined process for alkylation 100. The ethylene feed stream 105 is sent to the high-temperature alkylation reactor 110 along with an isoparaffin feed stream 115 comprising isobutane which react in the presence of an ionic liquid catalyst.

The effluent stream 120 from the high-temperature alkylation reactor 110 comprises alkylate, unreacted isoparaffin, and the ionic liquid catalyst. A portion 125 of the effluent stream 120 is recycled to the high-temperature reactor 110. In some cases, it may be desirable to control the temperature of the portion 125 of the effluent stream 120, such as by increasing the temperature to the desired range in a heater or heat exchanger 130.

The $C_3$-$C_5$ olefin feed stream 135 is sent to the low-temperature alkylation reactor 140 where it is reacted with the isoparaffin feed stream 115 comprising isobutane in the presence of the ionic liquid catalyst.

The effluent stream 145 from the low-temperature alkylation reactor 140 comprises alkylate, unreacted isoparaffin, and ionic liquid catalyst. A portion 150 of the effluent stream 145 is recycled to the low-temperature reactor 140. In some cases, it may be desirable to control the temperature of the recycle stream 150, such as by decreasing the temperature of the portion 150 to the desired range in a chiller 155.

A second portion 160 of the reactor effluent stream 120 and a second portion 165 of the reactor effluent stream 145 are sent to an ionic liquid separation zone 170 where the ionic liquid is separated from the alkylate and unreacted isoparaffin.

The hydrocarbon stream 175 from the ionic liquid separation zone 170 comprising the alkylate and unreacted isoparaffin is sent to the hydrocarbon separation zone 180 where it is separated into an isoparaffin recycle stream 185 comprising unreacted isoparaffin and an alkylate product stream 190 comprising alkylate.

The alkylate product stream 190 is recovered. The isoparaffin recycle stream 185 may be recycled to the high-temperature alkylation reactor 110, the low-temperature alkylation reactor 140, or both.

The ionic liquid recycle stream 195 from the ionic liquid separation zone 170 may be recycled to the high-temperature alkylation reactor 110, the low-temperature alkylation reactor 140, or both.

A portion 200 of the ionic liquid recycle stream 195 is sent to an ionic liquid regeneration zone 205 to remove conjunct polymer. The regenerated ionic liquid stream 210 may be combined with the ionic liquid recycle stream 195 and recycled to the high-temperature alkylation reactor 110, the low-temperature alkylation reactor 140, or both. During ionic liquid regeneration, conjunct polymer is cracked to gasoline boiling range hydrocarbons 215, which are removed from the ionic liquid regeneration zone 205 and combined with hydrocarbon stream 175.

EXAMPLES

Example 1: Ionic Liquid Catalyst

Various ionic liquid catalysts made of metal halides such as $AlCl_3$, $AlBr_3$, $GaCl_3$, $GaBr_3$, $InCl_3$, and $InBr_3$ could be used for the catalytic processes. N-butylpyridinium chloroaluminate ($C_5H_5NC_4H_9Al_2Cl_7$) ionic liquid catalyst was used in the following examples. The catalyst has the following composition:

| | |
|---|---|
| Wt % Al | 12.4 |
| Wt % Cl | 56.5 |
| Wt % C | 24.6 |
| Wt % H | 3.2 |
| Wt % N | 3.3 |

Example 2: Alkylation Process and Feeds Used

To a 100-1,000 mL Parr autoclave reactor, isobutane controlled by a Quizix pump, ethylene (Ultra-High-Purity (UHP) grade purchased from Airgas) controlled by a Bronkhorst flow controller, HCl promoter controlled by a Bronkhorst flow controller, and ionic liquid catalyst controlled by a LEWA pump were continuously fed. Both hydrocarbon feed and HCl promoter were fed to the top of reactor and ionic liquid was fed to the bottom of reactor. The reactor content was heated to the target temperature under the target pressure with overhead stirring. The target process conditions are shown in the Examples. The reactor effluent was taken from the top of the reactor. The reactor effluent was separated in a downstream separator into a separate product phase and an ionic liquid catalyst phase. The product was analyzed by gas chromatography.

Table 1 shows the composition of the isobutane and ethylene feeds used. FIG. 1 shows simplified process flow diagram for alkylation of ethylene with isobutane.

TABLE 1

Composition of isobutane and ethylene feeds

| | wt % |
|---|---|
| Isobutane (Refinery FCC) | |
| $C_3$ | 6.3 |
| $i-C_4$ | 79.9 |
| $n-C_4$ | 12.4 |
| $i-C_5$ | 1.4 |
| SUM | 100.0 |
| UHP-grade ethylene purchased from Airgas | |
| $C_{2=}$ | 99.9 |

Example 3: Alkylation of $C_3/C_4$ Olefin with Isobutane to Make Alkylate Gasoline Refinery isobutane containing 85% isobutane and 15% n-butane was used for this study after drying with 13X molecular sieve. A refinery olefin stream containing $C_3$ and $C_4$ olefins ($C_3/C_4$ olefin) from a Fluid Catalytic Cracking Unit (FCC) was dried with 13X molecular sieve and isomerized with a $Pd/Al_2O_3$ catalyst at 150° F., 250 psig in the presence of hydrogen to produce isomerized $C_3$ and $C_4$ olefin feed with the composition shown in Table 2.

TABLE 2

Composition of $C_3/C_4$ Olefin Feed

| Composition | Mol % |
|---|---|
| Propane, $C_3$ | 13.3 |
| Propylene, $C_{3=}$ | 25.4 |
| 1-Butene, $1-C_{4=}$ | 2.3 |
| 2-Butene, $2-C_{4=}$ | 16.2 |
| Isobutylene, $i-C_{4=}$ | 6.7 |
| n-Butane, $n-C_4$ | 12.4 |
| Isobutane, $i-C_4$ | 22.2 |
| $C_{5+}$ | 1.6 |
| Sum | 100.0 |

Evaluation of $C_3/C_4$ olefins alkylation with isobutane was performed in a continuously stirred tank reactor. An 8:1 molar mixture of isobutane and olefin was fed to the reactor while vigorously stirring. An ionic liquid catalyst was fed to the reactor via a second inlet port targeting to occupy 6 vol % in the reactor. A small amount of n-butyl chloride was added to produce anhydrous HCl gas. The average residence time (combined volume of feeds and catalyst) was about 12 minutes. The outlet pressure was maintained at 200 psig and the reactor temperature was maintained at 95° F. (35° C.) using external cooling.

The reactor effluent was separated with a coalescing separator into a hydrocarbon phase and an ionic liquid catalyst phase. The hydrocarbon stream was further separated into multiple streams with three distillation columns: a gas stream containing $C_3^-$ fraction, an $nC_4$ stream, an $iC_4$ stream, and an alkylate stream. The ionic liquid catalyst was recycled back to the alkylation reactor for repeated use. To maintain the activity of the ionic liquid catalyst, a fraction of used ionic liquid catalyst was sent to a hydrogenation reactor for reduction of the conjunct polymer level in the ionic liquid catalyst. We maintained the conjunct polymer level of the ionic liquid catalyst at 2-6% and obtained good alkylate gasoline property (Example 3A). The amount of conjunct polymer in the ionic liquid catalyst was determined using an FT-IR quantitation method described in earlier application.

In typical $C_3$ and $C_4$ olefin alkylation with an ionic liquid catalyst, the olefin conversion is always 100% (Examples 3A through 3C). For $C_4$ olefin alkylation, lower reaction temperature is preferred as the low reaction temperature generates alkylate gasoline with higher octane numbers and with higher content of trimethyl pentanes (Example 3B vs. 3C). Trimethyl pentanes are the most desirable component in the alkylate made from $C_4$ olefins with a research octane number of more than 100.

Example 4: Comparison of C2 Olefin Alkylation

A new ethylene alkylation process has been developed that will produce greater than 100 RON alkylate via direct alkylation of ethylene with isobutane using an ionic liquid catalyst. High activity of ionic liquid catalyst allows direct conversion of isobutane with ethylene to make alkylate gasoline comprising predominantly $C_6$ and $C_8$ paraffins. Conventional acids such as HF and $H_2SO_4$ cannot do this chemistry. Compared with $C_3$ and $C_4$ olefin alkylation with isobutane catalyzed with ionic liquid catalyst, $C_2$ olefin alkylation makes higher octane alkylate. This has not been discovered before. $C_2$ olefin alkylation with $iC_5$ was reported earlier (U.S. Pat. No. 7,432,408 Timken et. al.) where an RON of only 87 was reported.

TABLE 3

Comparison of $C_2$ Olefin Alkylation

|  | Example 4A (Invention) $C_2$ olefin alkylation with $iC_4$ Current Invention | Example 4B (Comparative) $C_2$ olefin alkylation with $iC_5$ U.S. Pat. No 7,432,408 |
|---|---|---|
| Alkylation temp (° F.) | 140 | 122 |
| Alkylation pressure (psig) | 400 | 300 |
| Isobutane/Olefin (molar) | 8 | 4 |
| Ionic liquid content (vol %) | 10 | 15 |
| Alky res. time (mins) | 8 | 40 |
| Olefin/Cl (molar) | 30 | — |
| Olefin Conversion (%) | 98.0 | 95.0 |
| Alkylate properties |  |  |
| $C_5$ Selectivity (%) | 0.9 | 4.1 ($C_{5-}$) |
| $C_6$ Selectivity (%) | 87.2 | 8.0 |
| $C_7$ Selectivity (%) | 1.1 | 63.3 |
| $C_8$ Selectivity (%) | 8.1 | 9.1 |
| $C_9$ Selectivity (%) | 0.3 | 7.1 |
| $C_{10}$ Selectivity (%) | 1.0 | 4.2 |
| $C_{11}$ Selectivity (%) | 0.7 | 4.3 ($C_{11+}$) |
| $C_{12}+$ Selectivity (%) | 0.8 |  |
| Sum (%) | 100.0 | 100.0 |
| RON | 101 | 87 |
| MON | 93.8 | 84 |
| FBP (99.5) (° F.) | 356 |  |

Example 5: $C_2$ Olefin Alkylation with $iC_4$

This process chemistry is unique and can be achieved with highly active ionic liquid catalysts at carefully controlled process conditions. Unlike $C_3$ to $C_4$ olefin alkylation processes, achieving ethylene conversion over 95% was very difficult. Unconverted ethylene stays as ethylene. This is very different from $C_3$ and $C_4$ olefin alkylation where at all conditions nearly 100% conversion of $C_3$ and $C_4$ olefins was achieved.

In the current invention, with carefully selected and controlled process conditions, complete conversion of ethylene was achieved (e.g., greater than 98%). When temperature and pressure are not sufficiently high, however, ethylene conversion was only 38% and alkylate product quality was poor (lower octanes) (Example 5D). The reaction temperature should be above 100° F., and the reaction pressure should be above 300 psig for optimum ethylene alkylation. This shows that the process conditions must be carefully selected.

TABLE 4

$C_2$ Olefin Alkylation Process and Properties of Alkylate Gasoline Produced

|  | Example 5A | Example 5B | Example 5C | Example 5D |
|---|---|---|---|---|
| Alkylation temp (° F.) | 140 | 120 | 100 | 90 |
| Alkylation pressure (psig) | 400 | 400 | 400 | 180 |

TABLE 4-continued $C_2$ Olefin Alkylation Process and Properties of Alkylate Gasoline Produced

|  | Example 5A | Example 5B | Example 5C | Example 5D |
|---|---|---|---|---|
| Isobutane/Olefin (molar) | 8 | 8 | 8 | 8 |
| Ionic liquid content (vol %) | 10 | 10 | 10 | 10 |
| Alky res. time (mins) | 8 | 8 | 10 | 6 |
| Olefin/Cl (molar) | 30 | 30 | 25 | 47 |
| $C_{2-}$ Conversion (%) | 98.0 | 96.0 | 99.7 | 38.0 |
| Alkylate properties |  |  |  |  |
| $C_5$ Selectivity (%) | 0.9 | 2.9 | 7.0 | 2.4 |
| $C_6$ Selectivity (%) | 87.2 | 85.1 | 71.4 | 55.9 |
| $C_7$ Selectivity (%) | 1.1 | 1.4 | 4.2 | 3.0 |
| $C_8$ Selectivity (%) | 8.1 | 6.9 | 10.0 | 26.3 |
| $C_9$ Selectivity (%) | 0.3 | 0.8 | 2.1 | 3.0 |
| $C_{10}$ Selectivity (%) | 1.0 | 1.3 | 2.6 | 4.7 |
| $C_{11}$ Selectivity (%) | 0.7 | 0.6 | 1.7 | 3.5 |
| $C_{12}+$ Selectivity (%) | 0.8 | 1.0 | 1.0 | 1.2 |
| Sum (%) | 100.0 | 100.0 | 100.0 | 100.0 |
| $C_6$ Isomers Distribution |  |  |  |  |
| 2,2-Di-Methyl-Butane/$C_6$ (%) | 0 | 1 | 2 | 0.3 |
| 2,3-Di-Methyl-Butane/$C_6$ (%) | 97 | 96 | 78 | 97 |
| 2-Methyl-Pentane/$C_6$ (%) | 2 | 3 | 12 | 2.8 |
| 3-Methyl-Pentane/$C_6$ (%) | 1 | 1 | 5 | 0 |
| Sum (%) | 100.0 | 100.0 | 100.0 | 100.0 |
| $C_8$ Isomers Distribution |  |  |  |  |
| Tri-Methyl-Pentanes/$C_8$ (%) | 70 | 68 | 53 | 47 |
| Di-Methyl-Hexanes/$C_8$ (%) | 21 | 19 | 34 | 50 |
| Methyl-Heptanes/$C_8$ (%) | 8 | 11 | 12 | 3 |
| Unknown/$C_8$ (%) | 0 | 0 | 0 | 0 |
| Sum (%) | 100.0 | 100.0 | 100.0 | 100.0 |
| RON (Based on GC) | 101.0 | 100.4 | 94.3 | 96.8 |
| MON (Based on GC) | 93.8 | 93.4 | 90.4 | 91.0 |
| SIMDIST (D2887) |  |  |  |  |
| T50 | 136 | 138 | 137 | 157 |
| T90 | 192 | 193 | 227 | 285 |
| T99 | 295 | 293 | 378 | 418 |
| FBP (99.5) | 356 | 363 | 423 | 441 |

For ethylene alkylation, the higher temperatures, 120° F. and above, generated alkylate with better octane numbers (Examples 5A and 5B vs. 5C and 5D). This is quite unexpected, and the opposite of the typical $C_4$ olefin alkylation, where the olefin conversion is always 100% and lower temperature gives better octane numbers (Examples 3B and 3C).

It was discovered that the alkylate gasoline produced by direct conversion of isobutane with ethylene by highly active ionic liquid catalyst was made of predominantly $C_6$ and $C_8$ paraffins. Conventional acids such as HF and $H_2SO_4$ cannot do this chemistry.

It was also discovered that product selectivity to $C_6$ alkylate (reaction product of 1 mole of ethylene and 1 mole of isobutane) and $C_8$ alkylate (reaction product of 2 moles of ethylene and 1 mole of isobutane) can be controlled. Different amounts of $C_6$ and $C_8$ can be produced depending on process conditions selected. The alkylate product was made of 70-90% $C_6$ and 6-30% $C_8$. The product contains very little $C_{12+}$.

Example 6: Composition of Alkylate Gasoline Made by Ethylene Alkylation with Isobutane It was discovered that, depending on the process conditions, the $C_8$ isomer composition varied significantly. $C_8$ isomers can be predominately trimethyl pentanes (high RON, 100-110 RON) or predominately dimethyl hexane (low RON, 56-76 RON).

At carefully selected process conditions, the $C_8$ isomer composition was made of predominantly, over 70%, trimethyl pentanes.

It was discovered that, at carefully selected process conditions, the $C_6$ composition was made of predominately, over 95%, 2,3-dimethyl butane (high RON, to 103.5 RON).

It was very surprising to discover that at a lower reaction temperature of 90° F. and a lower reaction pressure of 180 psig, the overall $C_6$ selectivity significantly decreased, and the $C_8$ selectivity significantly increased. Also, among $C_8$ isomers, di-methyl-hexanes significantly increased, and tri-methyl-pentanes significantly decreased, resulting in poor alkylate quality (lower octanes), clearly indicating that process conditions for ethylene alkylation must be carefully selected and controlled.

Our study above showed that we can make a new alkylate composition by ethylene alkylation with isobutane with an ionic liquid catalyst at the preferred process conditions. The composition of our alkylate of invention can be summarized as follows.

TABLE 5

| Features | Composition Range |
|---|---|
| Carbon number range | $C_5$-$C_{14}$ |
| Wt % $C_6$ | 70-90 |
| Wt % $C_8$ | 6-30 |
| Wt % $C_{12+}$ | <1 |
| 2,3-Dimethyl butane/Total $C_6$, % | 75-99 |
| Trimethyl pentanes/Total $C_8$, % | 50-80 |

The $C_2$ olefin alkylation can be processed in parallel with the $C_3$ to $C_5$ olefin alkylation with appropriate operating conditions for each reaction.

Example 7: Alkylation of C2 Olefin at Low Isobutane to Olefin Ratio

Two ethylene alkylation experiments were conducted to compare an isobutane to olefin molar ratio (I/O) with a molar I/O of 8 using a method similar to Example 2 above.

37.412 g/hr of 99.9% pure ethylene gas and 326 g/hr of liquid isobutane with about 95% purity were fed to the reactor to achieve a molar I/O of 4. Unreacted isobutane was separated from the alkylate product and recycled to the reactor. Ionic liquid catalyst, as described above, and n-butyl chloride were co-fed to the reactor with the ethylene and isobutane feeds. The results are summarized in Table 6, Examples 7a and 7b.

It was discovered that alkylation of $C_2$ olefins with ionic liquid has less of a dependence on the molar ratio of isobutane to olefin than alkylation of $C_3/C_4$ olefins. Namely, the alkylate quality and octane was not substantially reduced at lower isobutane to olefin ratios as compared to higher ratios, Example 7b. Additionally, the conjunct polymer rate in ethylene alkylation was not accelerated at the lower isobutane to olefin ratios as it is in some $C_3/C_4$ olefin alkylation reactions with ionic liquid. Conversion of the ethylene was not significantly affected, and conversions of greater than 98% were demonstrated. $C_6$ and $C_8$ selectivities remained relatively constant at the lower isobutane to olefin ratios as compared with alkylation at higher ratios.

There are several benefits to operating at a lower isobutane to olefin ratio, as it significantly reduces the amount of isobutane feed that must be fed to the alkylation reactor and recycled through the alkylation plant. This reduces the size of several pieces of equipment and lowers the operating duties resulting in more attractive economics for investment and operation.

TABLE 6

|  | Example 7a | Example 7b |
|---|---|---|
| Alkylation Temp (° F.) | 123.9 | 119.8 |
| Alkylation Pressure (psig) | 400 | 400 |
| Isobutane/Olefin (molar) | 4.0 | 8.1 |
| $C_{2-}$ Conversion (%) | 99.7 | 99.8 |
| Alkylate properties |  |  |
| $C_5$ Selectivity (%) | 0.00 | 0.00 |
| $C_6$ Selectivity (%) | 84.15 | 88.33 |
| $C_7$ Selectivity (%) | 1.96 | 1.16 |
| $C_8$ Selectivity (%) | 10.45 | 9.09 |
| $C_9$ Selectivity (%) | 2.58 | 1.14 |
| $C_{10}$ Selectivity (%) | 0.56 | 0.24 |
| $C_{11}$ Selectivity (%) | 0.25 | 0.04 |
| $C_{12+}$ Selectivity (%) | 0.06 | 0.00 |
| Sum (%) | 100 | 100 |
| RON (Based on GC) | 100.29 | 100.23 |
| MON (Based on GC) | 91.28 | 91.06 |
| FBP D2887 (99.5) (° F.) | 328.28 | 356 |

SPECIFIC EMBODIMENTS

While the following is described in conjunction with specific embodiments, it will be understood that this description is intended to illustrate and not limit the scope of the preceding description and the appended claims.

A first embodiment of the invention is a process for ionic liquid alkylation of $C_2$ to $C_5$ olefins comprising reacting an ethylene feed stream comprising ethylene and an isoparaffin feed stream comprising isobutane in the presence of an ionic liquid catalyst comprising an ionic liquid in a high-temperature alkylation reactor under first alkylation reaction conditions to form a first alkylation effluent stream comprising the first ionic liquid, the isoparaffin, and alkylate, wherein the first alkylation reaction conditions comprise a temperature in a range of 30° C. to 100° C. and a pressure in a range of 100 psig to 1000 psig; reacting a $C_3$-$C_5$ olefin feed stream comprising olefins having 3 to 5 carbon atoms and a second isoparaffin feed stream comprising isobutane in the presence of the ionic liquid catalyst in a low temperature alkylation reactor under second alkylation reaction conditions to form a second alkylation effluent stream comprising the second ionic liquid, the isoparaffin, and alkylate, wherein the second alkylation reaction conditions comprise a temperature in a range of 0° C. to 35° C. and a pressure in a range of 40 psig to 300 psig; combining a first portion of the first alkylation effluent stream and a first portion of the second alkylation effluent streams to form a combined stream; separating the combined stream into an ionic liquid recycle stream comprising the ionic liquid and a hydrocarbon stream comprising the isoparaffin and the alkylate; separating the hydrocarbon stream into an isoparaffin recycle stream comprising the isoparaffin and an alkylate stream comprising the alkylate; and recovering the alkylate stream. An embodiment of the invention is one, any or all of prior embodiments in this paragraph up through the first embodiment in this paragraph further comprising dividing the first alkylation effluent stream into the first portion and a second portion; heating the second portion of the first alkylation effluent stream and recycling the heated second portion of the first alkylation effluent stream to the high temperature alkylation reactor; dividing the second alkylation effluent stream into the first portion and a second portion; cooling the second portion of the second alkylation effluent stream and recycling the cooled second portion of the second alkylation effluent stream to the low temperature alkylation reactor. An embodiment of the invention is one, any or all of prior embodiments in this paragraph up through the first embodiment in this paragraph further comprising recycling the isoparaffin recycle stream to the high temperature alkylation reactor, the low temperature reactor, or both. An embodiment of the invention is one, any or all of prior embodiments in this paragraph up through the first embodiment in this paragraph further comprising recycling the ionic liquid recycle stream to the high temperature alkylation reactor, the low temperature reactor, or both. An embodiment of the invention is one, any or all of prior embodiments in this paragraph up through the first embodiment in this paragraph further comprising regenerating a portion of the ionic liquid recycle stream to form a regenerated ionic liquid stream; recycling the regenerated ionic liquid stream to the high temperature alkylation reactor, the low temperature reactor, or both. An embodiment of the invention is one, any or all of prior embodiments in this paragraph up through the first embodiment in this paragraph further comprising treating an ethylene stream to remove contaminants to form a treated ethylene stream, wherein the treated ethylene stream comprises the ethylene feed stream; and treating a $C_3$-$C_5$ olefin stream comprising olefins having 3 to 5 carbon atoms to remove contaminants to form a treated $C_3$-$C_5$ olefin stream, wherein the treated $C_3$-$C_5$ olefin stream comprises the $C_3$-$C_5$ olefin feed stream. An embodiment of the invention is one, any or all of prior embodiments in this paragraph up through the first embodiment in this paragraph, wherein the first alkylation reaction conditions comprise an overall paraffin to ethylene molar ratio of, and a residence time in a range of 5 minutes to 1 hr. An embodiment of the invention is one, any or all of prior embodiments in this paragraph up through the first embodiment in this paragraph, wherein the second alkylation reaction conditions comprise an overall paraffin to olefin molar ratio of 2:1 to 20:1, and a residence time in a range of 1 minute to 1 hr. An embodiment of the invention is one, any or all of prior embodiments in this paragraph up through the first embodiment in this paragraph wherein the ionic liquid comprises an organic cation and a halometallate anion and wherein the organic cation comprises an ammonium cation, a pyrrolidinium cation, a pyridinium cation, an imidazolium, a phosphonium cation, or a combination thereof. An embodiment of the invention is one, any or all of prior embodiments in this paragraph up through the first embodiment in this paragraph, wherein the ionic liquid comprises an organic cation and a halometallate anion and wherein the halometallate anion comprises a metal selected from Al, Ga, In, Mn, Fe, Co, Ni, Cu, Zn, or a combination thereof, and a halide selected from F, Cl, Br, I, or a combination thereof. An embodiment of the invention is one, any or all of prior embodiments in this paragraph up through the first embodiment in this paragraph wherein one or more of the ionic liquid is present in an amount of from 10 vol % to 60 vol % of a total volume of material in the high temperature alkylation reactor; the ionic liquid is present in an amount of from 1 vol % to 10 vol % of a total volume of material in the low temperature alkylation; and the ionic liquid is present in an amount of from 1 vol % to 60 vol % of a total volume of material in the combined stream. An embodiment of the invention is one, any or all of prior embodiments in this paragraph up through the first embodiment in this paragraph wherein the alkylate in the alkylate stream has a research octane number (RON) of 90 or more.

A second embodiment of the invention is a process for ionic liquid alkylation of $C_2$-$O_5$ olefins comprising reacting an ethylene feed stream comprising ethylene and an isoparaffin feed stream comprising isobutane with an ionic liquid catalyst comprising an ionic liquid in a high temperature alkylation reactor under first alkylation reaction conditions to form a first alkylation effluent stream comprising the first ionic liquid, the isoparaffin, and alkylate, wherein the first alkylation reaction conditions comprise a temperature in a range of 30° C. to 100° C., a pressure in a range of 100 psig to 1000 psig, an overall paraffin to ethylene molar ratio of 2:1 to 20:1, and a residence time in a range of 5 minutes to 1 hr; reacting a $C_3$-$C_5$ olefin feed stream comprising olefins having 3 to 5 carbon atoms and a second isoparaffin feed stream comprising isobutane with the ionic liquid catalyst in a low temperature alkylation reactor under second alkylation reaction conditions to form a second alkylation effluent stream comprising the second ionic liquid, the isoparaffin, and alkylate, wherein the second alkylation reaction conditions comprise a temperature in a range of 0° C. to 35° C., comprise a pressure in a range of 40 psig to 300 psig, an overall paraffin to olefin molar ratio of 2:1 to 20:1, and a residence time in a range of 1 minute to 1 hr; dividing the first alkylation effluent stream into a first portion and a second portion; heating the second portion of the first alkylation effluent stream and recycling the heated second portion of the first alkylation effluent stream to the high temperature alkylation reactor; dividing the second alkylation effluent stream into a first portion and a second portion; cooling the second portion of the second alkylation effluent stream and recycling the cooled second portion of the second alkylation effluent stream to the low temperature alkylation reactor; combining the first portion of the first alkylation effluent stream and the first portion of the second alkylation effluent streams to form a combined stream; separating the combined stream into an ionic liquid recycle stream comprising the ionic liquid and a hydrocarbon stream comprising the isoparaffin and the alkylate; separating the hydrocarbon stream into an isoparaffin recycle stream comprising the isoparaffin and an alkylate stream comprising the alkylate; recycling the isoparaffin recycle stream to the high temperature alkylation reactor, the low temperature reactor, or both; recycling the ionic liquid recycle stream to the high temperature alkylation reactor, the low temperature reactor, or both; and recovering the alkylate stream. An embodiment of the invention is one, any or all of prior embodiments in this paragraph up through the second embodiment in this paragraph further comprising regenerating a portion of the ionic liquid recycle stream to form a regenerated ionic liquid stream; recycling the regenerated ionic liquid stream to the high temperature alkylation reactor, the low temperature reactor, or both. An embodiment of the invention is one, any or all of prior embodiments in this paragraph up through the second embodiment in this paragraph further comprising treating an ethylene stream to remove contaminants to form a treated ethylene stream, wherein the treated ethylene stream comprises the ethylene feed stream; treating a $C_3$-$C_5$ olefin stream comprising olefins having 3 to 5 carbon atoms to remove contaminants to form a treated $C_3$-$C_5$ olefin stream, wherein the treated $C_3$-$C_5$ olefin stream comprises the $C_3$-$C_5$ olefin feed stream. An embodiment of the invention is one, any or all of prior embodiments in this paragraph up through the second embodiment in this paragraph wherein the ionic liquid comprises an organic cation and a halometallate anion and wherein the organic cation comprises an ammonium cation, a pyrrolidinium cation, a pyridinium cation, an imidazolium, a phosphonium cation, or a combination thereof. An embodiment of the invention is one, any or all of prior embodiments in this paragraph up through the second embodiment in this paragraph wherein the ionic liquid comprises an organic cation and a halometallate anion and wherein the halometallate anion comprises a metal selected from Al, Ga, In, Mn, Fe, Co, Ni, Cu, Zn, or a combination thereof, and a halide selected from F, Cl, Br, I, or a combination thereof. An embodiment of the invention is one, any or all of prior embodiments in this paragraph up through the second embodiment in this paragraph wherein one or more of the ionic liquid is present in an amount of from 10 vol % to 60 vol % of a total volume of material in the high temperature alkylation reactor; the ionic liquid is present in an amount of from 1 vol % to 10 vol % of a total volume of material in the low temperature alkylation; and the ionic liquid is present in an amount of from 1 vol % to 60 vol % of a total volume of material in the combined stream. An embodiment of the invention is one, any or all of prior embodiments in this paragraph up through the second embodiment in this paragraph wherein the alkylate in the alkylate stream has a research octane number (RON) of 90 or more.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. An integrated process for ionic liquid alkylation of $C_2$ to $C_5$ olefins comprising:

reacting an ethylene feed stream comprising ethylene and an isoparaffin feed stream comprising isobutane in the presence of an ionic liquid catalyst comprising an ionic liquid in a high-temperature alkylation reactor under first alkylation reaction conditions to form a first alkylation effluent stream comprising ionic liquid, isobutane, and alkylate, wherein the first alkylation reaction conditions comprise a temperature in a range of 30° C. to 100° C. and a pressure in a range of 100 psig to 1000 psig;

reacting a $C_3$-$C_5$ olefin feed stream comprising olefins having 3 to 5 carbon atoms and a second isoparaffin feed stream comprising isobutane in the presence of a second ionic liquid catalyst comprising ionic liquid in a low temperature alkylation reactor under second alkylation reaction conditions to form a second alkylation effluent stream comprising ionic liquid, isobutane, and alkylate, wherein the second alkylation reaction conditions comprise a temperature in a range of 0° C. to 35° C. and a pressure in a range of 40 psig to 300 psig;

combining a first portion of the first alkylation effluent stream and a first portion of the second alkylation effluent streams to form a combined stream;

separating the combined stream into an ionic liquid recycle stream comprising ionic liquid and a hydrocarbon stream comprising isobutane and alkylate;

separating the hydrocarbon stream into an isoparaffin recycle stream comprising isobutane and an alkylate stream comprising alkylate; and recovering the alkylate stream.

2. The process of claim 1 further comprising:

dividing the first alkylation effluent stream into the first portion and a second portion;

heating the second portion of the first alkylation effluent stream and recycling the heated second portion of the first alkylation effluent stream to the high temperature alkylation reactor;

dividing the second alkylation effluent stream into the first portion and a second portion; and cooling the second portion of the second alkylation effluent stream and recycling the cooled second portion of the second alkylation effluent stream to the low temperature alkylation reactor.

3. The process of claim 1 further comprising:

recycling the isoparaffin recycle stream to the high temperature alkylation reactor, the low temperature reactor, or both.

4. The process of claim 1 further comprising:

recycling the ionic liquid recycle stream to the high temperature alkylation reactor, the low temperature reactor, or both.

5. The process of claim 1 further comprising:

regenerating a portion of the ionic liquid recycle stream to form a regenerated ionic liquid stream; and recycling the regenerated ionic liquid stream to the high temperature alkylation reactor, the low temperature reactor, or both.

6. The process of claim 1 further comprising:

treating an ethylene stream to remove contaminants to form a treated ethylene stream, wherein the treated ethylene stream comprises the ethylene feed stream; and treating a $C_3$-$C_5$ olefin stream comprising olefins having 3 to 5 carbon atoms to remove contaminants to form a treated $C_3$-$C_5$ olefin stream, wherein the treated $C_3$-$C_5$ olefin stream comprises the $C_3$-$C_5$ olefin feed stream.

7. The process of claim 1, wherein the first alkylation reaction conditions comprise an overall paraffin to ethylene molar ratio of 2:1 to 20:1, and a residence time in a range of 5 minutes to 1 hr.

8. The process of claim 1, wherein the second alkylation reaction conditions comprise an overall paraffin to olefin molar ratio of 2:1 to 20:1, and a residence time in a range of 1 minute to 1 hr.

9. The process of claim 1 wherein the ionic liquid comprises an organic cation and a halometallate anion and wherein the organic cation comprises an ammonium cation, a pyrrolidinium cation, a pyridinium cation, an imidazolium, a phosphonium cation, or a combination thereof.

10. The process of claim 1, wherein the ionic liquid comprises an organic cation and a halometallate anion and wherein the halometallate anion comprises a metal selected from Al, Ga, In, Mn, Fe, Co, Ni, Cu, Zn, or a combination thereof, and a halide selected from F, Cl, Br, I, or a combination thereof.

11. The process of claim 1 wherein one or more of:
the ionic liquid is present in an amount of from 5 vol % to 60 vol % of a total volume of material in the high temperature alkylation reactor;
the ionic liquid is present in an amount of from 1 vol % to 10 vol % of a total volume of material in the low temperature alkylation; and
the ionic liquid is present in an amount of from 1 vol % to 60 vol % of a total volume of material in the combined stream.

12. The process of claim 1 wherein the alkylate in the alkylate stream has a research octane number (RON) of 90 or more.

13. An integrated process for ionic liquid alkylation of $C_2$ to $C_5$ olefins comprising:
reacting an ethylene feed stream comprising ethylene and an isoparaffin feed stream comprising isobutane with an ionic liquid catalyst comprising an ionic liquid in a high temperature alkylation reactor under first alkylation reaction conditions to form a first alkylation effluent stream comprising the first ionic liquid, the isoparaffin, and alkylate, wherein the first alkylation reaction conditions comprise a temperature in a range of 30° C. to 100° C., a pressure in a range of 100 psig to 1000 psig, an overall paraffin to ethylene molar ratio of 2:1 to 20:1, and a residence time in a range of 5 minutes to 1 hr;
reacting a $C_3$-$C_5$ olefin feed stream comprising olefins having 3 to 5 carbon atoms and a second isoparaffin feed stream comprising isobutane with the ionic liquid catalyst in a low temperature alkylation reactor under second alkylation reaction conditions to form a second alkylation effluent stream comprising the second ionic liquid, the isoparaffin, and alkylate, wherein the second alkylation reaction conditions comprise a temperature in a range of 0° C. to 35° C., comprise a pressure in a range of 40 psig to 300 psig, an overall paraffin to olefin molar ratio of 2:1 to 20:1, and a residence time in a range of 1 minute to 1 hr;
dividing the first alkylation effluent stream into a first portion and a second portion;
heating the second portion of the first alkylation effluent stream and recycling the heated second portion of the first alkylation effluent stream to the high temperature alkylation reactor;
dividing the second alkylation effluent stream into a first portion and a second portion;
cooling the second portion of the second alkylation effluent stream and recycling the cooled second portion of the second alkylation effluent stream to the low temperature alkylation reactor;
combining the first portion of the first alkylation effluent stream and the first portion of the second alkylation effluent streams to form a combined stream;
separating the combined stream into an ionic liquid recycle stream comprising the ionic liquid and a hydrocarbon stream comprising the isoparaffin and the alkylate;
separating the hydrocarbon stream into an isoparaffin recycle stream comprising the isoparaffin and an alkylate stream comprising the alkylate;
recycling the isoparaffin recycle stream to the high temperature alkylation reactor, the low temperature reactor, or both;
recycling the ionic liquid recycle stream to the high temperature alkylation reactor, the low temperature reactor, or both; and
recovering the alkylate stream.

14. The process of claim 13 further comprising:
regenerating a portion of the ionic liquid recycle stream to form a regenerated ionic liquid stream; and
recycling the regenerated ionic liquid stream to the high temperature alkylation reactor, the low temperature reactor, or both.

15. The process of claim 13 further comprising:
treating an ethylene stream to remove contaminants to form a treated ethylene stream, wherein the treated ethylene stream comprises the ethylene feed stream;
treating a $C_3$-$C_5$ olefin stream comprising olefins having 3 to 5 carbon atoms to remove contaminants to form a treated $C_3$-$C_5$ olefin stream, wherein the treated $C_3$-$C_5$ olefin stream comprises the $C_3$-$C_5$ olefin feed stream.

16. The process of claim 13 wherein the ionic liquid comprises an organic cation and a halometallate anion and wherein the organic cation comprises an ammonium cation, a pyrrolidinium cation, a pyridinium cation, an imidazolium, a phosphonium cation, or a combination thereof.

17. The process of claim 13 wherein the ionic liquid comprises an organic cation and a halometallate anion and wherein the halometallate anion comprises a metal selected from Al, Ga, In, Mn, Fe, Co, Ni, Cu, Zn, or a combination thereof, and a halide selected from F, Cl, Br, I, or a combination thereof.

18. The process of claim 13 wherein one or more of:
the ionic liquid is present in an amount of from 5 vol % to 60 vol % of a total volume of material in the high temperature alkylation reactor;
the ionic liquid is present in an amount of from 1 vol % to 10 vol % of a total volume of material in the low temperature alkylation; and
the ionic liquid is present in an amount of from 1 vol % to 60 vol % of a total volume of material in the combined stream.

19. The process of claim 13 wherein the alkylate in the alkylate stream has a research octane number (RON) of 90 or more.

* * * * *